United States Patent
Kim et al.

(10) Patent No.: US 9,532,753 B2
(45) Date of Patent: Jan. 3, 2017

(54) X-RAY IMAGING DEVICE

(71) Applicants: Vatech Co., Ltd., Gyeonggi-do (KR); Vatech Ewoo Holdings Co., Ltd., Gyeonggi-do (KR)

(72) Inventors: Tae Woo Kim, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 69 days.

(21) Appl. No.: 14/433,837

(22) PCT Filed: Oct. 4, 2013

(86) PCT No.: PCT/KR2013/008870
§ 371 (c)(1),
(2) Date: Apr. 6, 2015

(87) PCT Pub. No.: WO2014/054899
PCT Pub. Date: Apr. 10, 2014

(65) Prior Publication Data
US 2015/0238153 A1    Aug. 27, 2015

(30) Foreign Application Priority Data

Oct. 4, 2012  (KR) .................. 10-2012-0110220

(51) Int. Cl.
*A61B 6/00*    (2006.01)
*G01N 23/00*    (2006.01)
(Continued)

(52) U.S. Cl.
CPC ............. *A61B 6/06* (2013.01); *A61B 6/032* (2013.01); *A61B 6/035* (2013.01); *A61B 6/14* (2013.01);
(Continued)

(58) Field of Classification Search
USPC ........................... 378/8, 16, 87, 210
See application file for complete search history.

(56) References Cited

U.S. PATENT DOCUMENTS 7,103,139 B2 *  9/2006  Nagaoka ............... A61B 6/032
                                                378/16
7,269,242 B2 *  9/2007  Tanaka ................. A61B 6/0478
                                                378/16
(Continued)

FOREIGN PATENT DOCUMENTS

JP  11-253435 A    9/1999
JP  2007-236784 A  9/2007
(Continued)

OTHER PUBLICATIONS

Korean Intellectual Property Office, International Search Report for International Application No. PCT/KR2013/008870, Jan. 13, 2014.
(Continued)

*Primary Examiner* — Bernard Souw
(74) *Attorney, Agent, or Firm* — IP Legal Services, LLC

(57) ABSTRACT

The purpose of the present invention is to provide an X-ray imaging device capable of obtaining more diversified X-ray image information. To this end, the present invention comprises: an X-ray generation device for generating an X-ray; an X-ray detection device for detecting the X-ray which is generated in the X-ray generation device and penetrates the subject; and a collimator arranged between the X-ray generation device and the X-ray detection device, wherein the X-ray detection device and/or the collimator provides an X-ray imaging device configured to rotate relative to the X-ray generation device. Thus, since it is possible to adjust an X-ray detection area if necessary, the visual field of the imaging device can be adjusted such that diversified X-ray image information can be obtained.

10 Claims, 4 Drawing Sheets

(51) Int. Cl.
*H05G 1/60* (2006.01)
*A61B 6/06* (2006.01)
*A61B 6/14* (2006.01)
*A61B 6/03* (2006.01)

(52) U.S. Cl.
CPC .......... *A61B 6/4441* (2013.01); *A61B 6/4452* (2013.01); *A61B 6/501* (2013.01)

(56) References Cited

U.S. PATENT DOCUMENTS

| | | | | |
|---|---|---|---|---|
| 7,522,696 | B2* | 4/2009 | Imai | A61B 6/032 378/15 |
| 7,734,009 | B2* | 6/2010 | Brunner | A61B 6/466 378/15 |
| 8,279,998 | B2* | 10/2012 | Kobayashi | A61B 6/032 378/8 |
| 8,848,861 | B2* | 9/2014 | Hall | A61B 6/03 378/8 |
| 2005/0074087 | A1 | 4/2005 | Nukui | |
| 2014/0205060 | A1* | 7/2014 | Kim | A61B 6/4233 378/20 |
| 2014/0355735 | A1* | 12/2014 | Choi | A61B 6/544 378/8 |
| 2015/0085972 | A1* | 3/2015 | Choi | A61B 6/541 378/8 |
| 2016/0148399 | A1* | 5/2016 | Kim | G06T 11/006 382/131 |
| 2016/0151027 | A1* | 6/2016 | Yoshikawa | A61B 6/4035 378/16 |

FOREIGN PATENT DOCUMENTS

JP 2007-301409 A 11/2007
JP 2008-036272 A 2/2008

OTHER PUBLICATIONS

Korean Intellectual Property Office, Written Opinion of the International Searching Authority for International Application No. PCT/KR2013/008870, Jan. 13, 2014.

* cited by examiner

X-RAY IMAGING DEVICE

CROSS REFERENCE TO RELATED APPLICATIONS

This application is a National Stage Patent Application of PCT International Patent Application No. PCT/KR2013/008870 (filed on Oct. 4, 2013) under 35 U.S.C. §371, which claims priority to Korean Patent Application No. 10-2012-0110220 (filed on Oct. 4, 2012), the teachings of which are incorporated herein in their entireties by reference.

TECHNICAL FIELD

The present invention relates to an X-ray imaging device and, more particularly, to an X-ray imaging device available for various usages because of an adjustable field of view.

BACKGROUND ART

X-ray imaging devices in the field of dental treatment can be classified into a CT scanner, a panoramic imaging device, and a cephalometric device, and appropriate devices are selected and used in accordance with the diagnosis purposes.

Of these devices, the panoramic imaging device is most frequently used for the characteristics of dental treatment. The panoramic imaging device takes tomographic images while rotating along a necessary locus to fit to the shape of a dental arch and these images are connected, so a planar panoramic image is obtained.

For the characteristics of the panoramic imaging device, it is possible to use an X-ray detection sensor with a small area relative to the CT scanner.

In this respect, the CT scanner requires a plane type detection sensor with a large area for its characteristics, but the panoramic imaging device can use a line type detection sensor extending in one direction.

As described above, the panoramic imaging device can use an expensive detection sensor in a small area, so it has the advantage that the manufacturing cost is reduced.

Panoramic imaging devices of the related art, however, use line type detectors in a fixed state. Accordingly, the fields of view (FOV) of the imaging devices are also fixed, so the obtained image information is necessarily limited.

Such a functional limit exists in the X-ray imaging device as well other than the panoramic imaging device.

Therefore, an X-ray imaging device capable of obtaining a wider range of X-ray image information is strongly required.

DISCLOSURE

Technical Problem

An object of the present invention is to provide an X-ray imaging device capable of obtaining a wider range of X-ray image information.

Technical Solution

In order to achieve the object, the present invention provides an X-ray imaging device including: an X-ray generator for generating an X-ray; an X-ray detector for detecting an X-ray generated by the X-ray generator and passing through an object; and a collimator disposed between the X-ray generator and the X-ray detector, in which at least one of the X-ray detector or the collimator is rotated relative to the X-ray generator.

At least one of the X-ray detector and the collimator may be rotated about a rotation axis directing the X-ray generator. At least one of the rotation axis and the X-ray detector or the rotation axis and the X-ray generator may maintain an angle that exceeds 0 degrees and is 90 degrees or less. At least one of angles made by the rotation axis and the X-ray detector or the rotation angle and the X-ray generator may be fixed or changed during imaging. The relative rotation may be made while X-ray imaging is performed or until imaging is finished from before X-ray imaging. The X-ray detector or the collimator may be adjusted in position in a height direction or a width direction relative to the X-ray generator. A rotation axis for the relative rotation may be positioned inside the X-ray detector or the collimator. The X-ray imaging device may include a rotary arm having the X-ray generator and the X-ray detector at both ends and rotating. Both of the X-ray detector and the collimator may be rotated about a rotation axis directing the X-ray generator. The X-ray imaging device may produce at least one of a CT image, a panoramic image, and a cephalometric image.

Advantageous Effects

According to the present invention, it is possible to rotate and/or adjust the position of one of an X-ray detector and a collimator, which are main components of an X-ray imaging device, relative to the other. Accordingly, it is possible to adjust the X-ray detection area, if necessary. Therefore, it is possible to adjust the field of view of the imaging device, so it is possible to obtain a wider range of X-ray image information.

MODE FOR INVENTION

Hereinafter, embodiments of the present invention will be described in detail with reference to the drawings.

Figure 1:
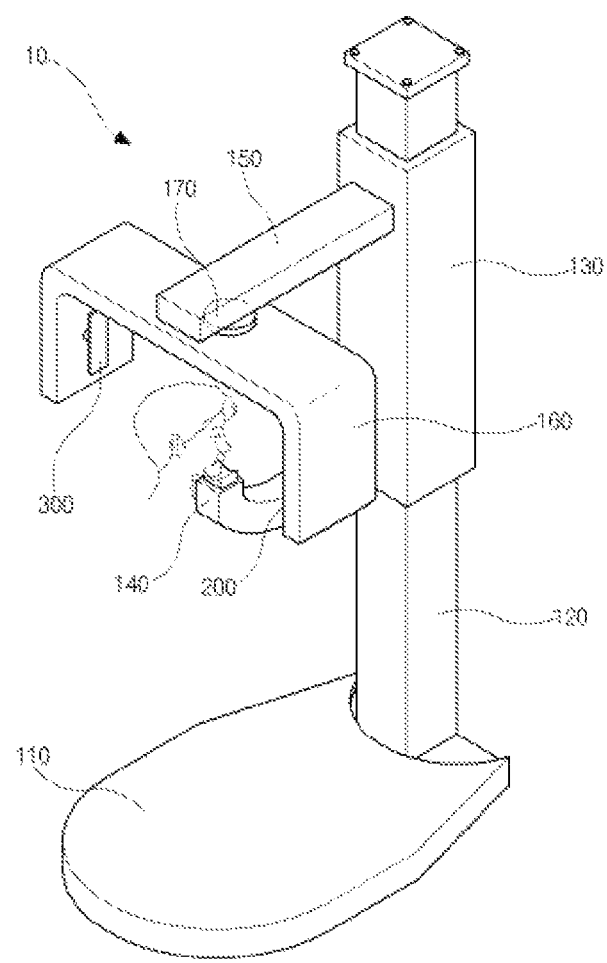
FIG. 1 is a perspective view schematically showing an X-ray imaging device according to a first embodiment of the present invention.
Figure 2:
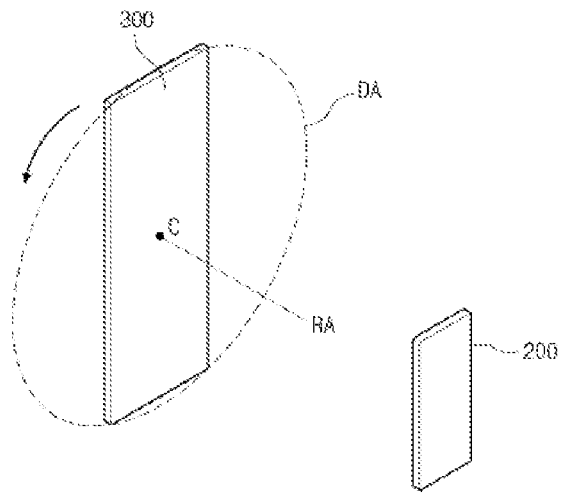
FIG. 2 is a view schematically showing rotation of an X-ray detector according to the first embodiment of the present invention.

FIG. 1 is a perspective view schematically showing an X-ray imaging device according to a first embodiment of the present invention and FIG. 2 is a view schematically showing rotation of an X-ray detector according to the first embodiment of the present invention.

An X-ray imaging device 10 according to an embodiment of the present invention may be any X-ray imaging devices that are used in various ways and for various purposes.

Various X-ray imaging devices, for example, a CT scanner, a panoramic imaging device, and a cephalometric device may be used. A dental X-ray imaging device is exemplified for the X-ray imaging device in the following description for the convenience of description. Such an X-ray imaging device may be configured to produce, for example, at least one of a CT image, a panoramic image, and a cephalometric image.

Referring to FIGS. 1 and 2, the X-ray imaging device 10 according to a first embodiment of the present invention may include a base 110, a support 120, a lifting member 130, a jaw holder 130, a rotary arm support 150, a rotary arm 160, a rotary arm driving unit 170, an X-ray generator 200, and an X-ray detector 300.

The base 110 is placed on the floor and holds the support 120 with the components.

The support 120 is connected to the base 110 and vertically extends in an upright position from the base 110.

The lifting member 130 is mounted on the support 120 and moved up/down along the support 120 by a driving unit such as a motor. By these motions, it is possible to adjust the height of the jaw holder 140 to fit to the height of a patient who is an examinee.

The jaw holder 140 is mounted on the lifting member 130 and holds the patient's jaw. By the jaw holder 140, the head of an examinee, that is, an object can be positioned between the X-ray generator and the X-ray detector 300. In this configuration, if necessary, a headrest (not shown) that is mounted on the rotary arm 160 may be used instead of the jaw holder 140.

The rotary arm support 150 is connected to the upper portion of the lifting member 130 and extends in parallel with the floor. The rotary arm 160 is connected to the bottom of the rotary arm support 150.

The rotary arm 160 connected in this way can be moved horizontally in parallel with the floor or rotated about an axis perpendicular to the floor by the rotary arm driving unit 170.

The rotary arm 160 may have a horizontal part connected to the rotary arm support 150 and vertical parts bending down at both ends of the horizontal part.

The X-ray generator 200 and the X-ray detector 300 that face each other may be disposed on the inner sides of the vertical parts of the rotary arm 160.

The X-ray generator 200 is a component for generating and radiating an X-ray to an object and the radiated X-ray travels to the X-ray detector 300 through the object.

The X-ray detector 300 may include a detection panel and a driving circuit for driving the detection panel.

A plurality of detection pixels are arranged in a matrix in the detection panel. The detection pixels convert an X-ray into an electric detection signal and the detection signal is transmitted to the driving circuit. The detection panel has a rectangular shape in a plane, and for example, a line type detector extending in one direction may be used, but the present invention is not limited thereto and a plane type detector may be used as another example.

The driving circuit processes the detection signal and then transmits it to a diagnosis computer. The diagnosis computer analyzes the detection signal and produces an X-ray image and the X-ray image is displayed by a display device and can be used as an image for diagnosis.

On the other hand, the X-ray detector 300 according to the first embodiment of the present invention can rotate relative to the X-ray generator 200. When it is rotated, an X-ray detection area is enlarged, and accordingly, the field of vision of the X-ray imaging device can be enlarged. This configuration is described in more detail with reference to FIG. 2.

Referring to FIG. 2, the X-ray detector 300 can be rotated relative to the X-ray generator 200, with a rotation axis directing the X-ray generator 200. If necessary, at least one of the angles made by the rotation axis and the X-ray generator 200 or the rotation axis and the X-ray detector 300 is not necessarily a right angle and may be adjusted within a range over 0 degree where they are parallel with each other to 90 degrees where they are perpendicular to each other. Further, at least one of the angles made by the rotation axis and the X-ray generator 200 or the rotation axis and the X-ray detector 300 may be changed or fixed during imaging. For the convenience of description, it is exemplified that the X-ray detector 300 rotates and the X-ray generator 200 is fixed, in which the X-ray detector 300 is a line type X-ray detector.

The X-ray detector 300 may be arranged with a longitudinal long axis substantially perpendicular to the floor, for example, in a normal operation mode that is a general operation mode. In this state, for example, when the rotary arm 160 is rotated about its rotation axis, a panorama image in the normal operation mode can be obtained.

In a rotation mode in which the X-ray detector 300 is rotated, the X-ray detector 300 is rotated about a rotation axis RA directing the X-ray generator 200. Accordingly, a circular rotation area can be defined by the X-ray detector 300. The rotation area functions as an actual detection area DA for detecting X-rays.

As described above, as the X-ray detector 300 is rotated, the X-ray detection area DA larger than area in a fixed state can be defined. Therefore, the field of view of the X-ray imaging device 10 is enlarged, so X-ray images with more information can be obtained.

X-ray imaging in the rotation mode of the X-ray detector 300 can be performed while the rotary arm 160 is rotated or stopped, depending on the diagnosis purposes.

It is preferable that the rotation axis RA of the X-ray detector 300 is positioned in the plane of the X-ray detector 300, and the position of the rotation axis RA may be the center C of the X-ray detector 300 or the other positions.

Figure 3:
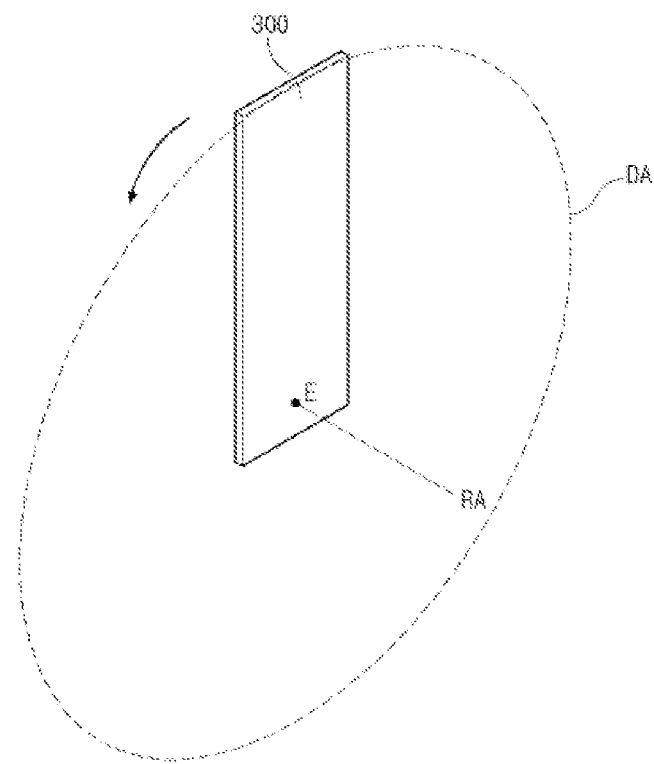
FIG. 3 is a view schematically showing eccentric rotation of the X-ray detector according to the first embodiment of the present invention.

FIGS. 2 and 3 can be referred to for this configuration. FIG. 2 shows centric rotation when the rotation axis RA is positioned at the center C of the X-ray detector 300 and FIG. 3 shows eccentric rotation when the rotation axis RA is positioned at a point E under the center C.

The first embodiment of the present invention may include a case when the rotation area is adjusted by adjusting the position of the rotation axis C.

Figure 4:
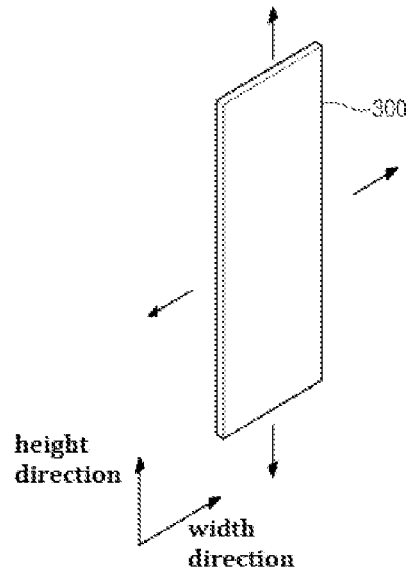
FIG. 4 is a view schematically showing a motor for adjusting a position of the X-ray detector according to the first embodiment of the present invention.

The position of the X-ray detector 300 may be adjusted relative to the X-ray generator 200. For example, as shown in FIG. 4, the X-ray detector 300 may be freely moved up and down or left and right. By this adjustment, the position of the X-ray detection area can be adjusted. Accordingly, various X-ray images can be obtained.

The position adjustment of the X-ray detector 300 may be performed before or during X-ray imaging. Further, the X-ray imaging performed with the position adjustment of the X-ray detector 300 may be performed while the rotary arm 160 is rotated or stopped.

In order to rotate or adjust the portion of the X-ray detector 300, as described above, the X-ray imaging device 10 may be equipped with a driving unit that supplies power to the X-ray detector 300. It is preferable to mount the driving unit on the rotary arm 160, but the present invention is not limited thereto.

In the above description, it was exemplified that X-ray imaging is performed with the X-ray detector 300 vertically arranged. However, X-ray imaging may be performed with the X-ray detector 300 in parallel with the floor or at an angle from the floor.

The X-ray detector 300 can be arranged to be vertical, horizontal, and inclined, for example, by rotating the X-ray detector 300 before X-ray imaging.

As described above, the X-ray detector according to the first embodiment of the present invention can be relatively rotated. Accordingly, it is possible to adjust the X-ray detection area, if necessary. Therefore, it is possible to adjust the field of view of the imaging device, so it is possible to obtain various items of X-ray information.

Figure 5:
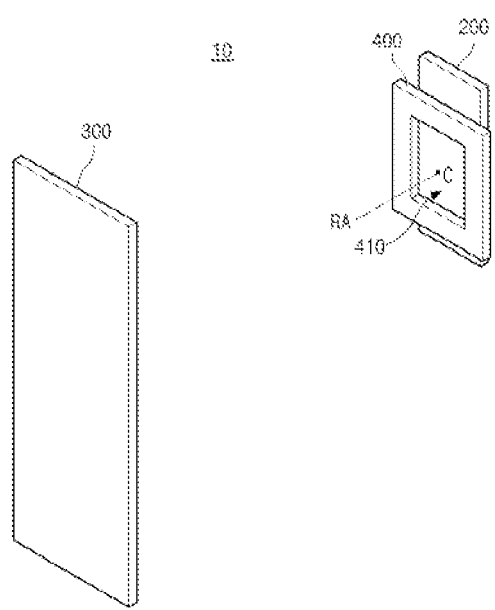
FIG. 5 is a perspective view schematically showing an X-ray imaging device using a collimator according to a second embodiment of the present invention.
Figure 6:
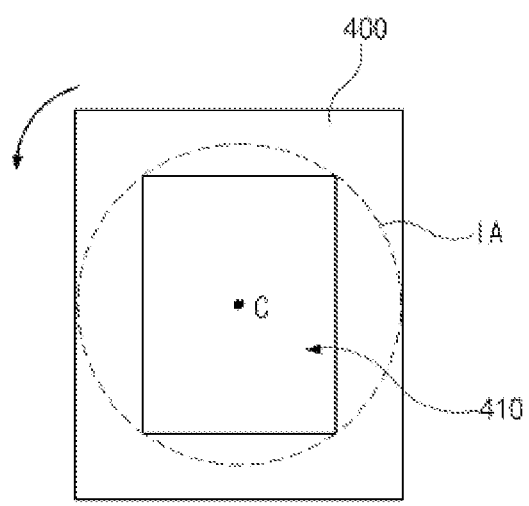
FIG. 6 is a view schematically showing rotation of the collimator according to the second embodiment of the present invention.

An X-ray imaging device according to a second embodiment of the present invention is described hereafter with reference to FIGS. 5 and 6. FIG. 5 is a perspective view schematically showing an X-ray imaging device using a collimator according to a second embodiment of the present invention and FIG. 6 is a view schematically showing rotation of the collimator according to the second embodiment of the present invention.

In the second embodiment, for the convenience of description, the configurations the same as or similar to those of the first embodiment may not be described.

Referring to FIGS. 5 and 6, the X-ray imaging device according to the second embodiment may further include a collimator that can be rotated with respect to the X-ray generator 200 or the X-ray detector 300.

If necessary, at least one of the angles made by the rotation axis of the collimator 400 and the X-ray generator 200 or the X-ray detector 300 is not necessarily a right angle and may be adjusted within a range over 0 degree where they are parallel with each other to 90 degrees where they are perpendicular to each other. Further, at least one of the angles made by the rotation axis and the X-ray generator 200 or the rotation axis and the X-ray detector 300 may be changed or fixed during imaging.

It is exemplified in the second embodiment that, for the convenience of description, the X-ray generator 200 and the X-ray detector 300 are fixed and the collimator 400 is rotated.

The collimator 400, a part for determining an X-ray radiation area, functions as an X-ray mask. To this end, the collimator 400 has an opening 410 therein through which an X-ray passes.

The collimator 400 may be composed of one or a plurality of frames. When it is composed of a plurality of frames, the area of the opening 410 may be adjusted.

The collimator 400 is disposed between the X-ray generator 200 and the X-ray detector 300, and preferably, it is disposed ahead of the X-ray generator 200 or the X-ray detector 300. In the second embodiment, it is exemplified that it is disposed ahead of the X-ray generator 200.

The collimator 400 is not rotated, but stopped in a normal operation mode that is a general operation mode. In this state, for example, when the rotary arm 160 (see FIG. 1) is rotated about its rotation axis, the collimator 400 is rotated accordingly, so a panoramic image in the normal operation mode can be obtained.

The collimator 400 operates similar to the X-ray detector 300 of the first embodiment, in the rotation mode.

That is, the collimator 400 is rotated about a rotation axis RA directing the X-ray generator 200 or the X-ray detector 300. Accordingly, a circular rotation area can be defined by the opening 410 of the collimator. The rotation area functions as an actual radiation area IA to which X-rays are radiated.

As described above, as the collimator 400 is rotated, the X-ray detection area IA larger than area in a fixed state can be defined. This consequently means enlargement of an area for detecting X-rays. Therefore, the view of the X-ray imaging device 10 is enlarged, so X-ray images with more information can be obtained.

X-ray imaging in the rotation mode of the collimator 400 may be performed while the rotary arm is rotated or stopped, depending on the diagnosis purposes.

It is preferable that the rotation axis RA of the collimator 400 is positioned within the plane of the collimator 400, and the position of the rotation axis RA may be the center C of the collimator 400 or other points.

In this respect, the collimator 400 centrically rotates when the rotational axis RA is positioned at the center C, but it eccentrically rotate when the rotational axis RA is not positioned at the center C, but at other points.

The second embodiment of the present invention may include a case when the rotation area is adjusted by adjusting the position of the rotational axis C.

The position of the collimator 400 may be adjusted relative to the X-ray generator 200 or the X-ray detector 300. For example, the collimator 400 can be freely moved up and down and left and right. By this adjustment, the position of the X-ray radiation area can be adjusted. Accordingly, various X-ray images can be obtained.

The position adjustment of the collimator 400 may be performed before or during X-ray imaging. Further, X-ray imaging that is performed with the position adjustment of the collimator 400 may be performed while the rotary arm is rotated or stopped, depending on the diagnosis purposes.

In order to rotate or adjust the portion of the collimator 400, as described above, the X-ray imaging device 10 may be equipped with a driving unit that supplies power to the collimator 400. It is preferable to mount the driving unit on the rotary arm, but the present invention is not limited thereto.

Further, X-ray imaging may be performed with the collimator 400 arranged in parallel with or at an angle with the floor. It is possible to adjust the collimator 400 to be parallel or inclined, for example, by rotating the collimator 400 before X-ray imaging.

As described above, the collimator according to the second embodiment of the present invention can be relatively rotated. Accordingly, the X-ray detection area can be adjusted, if necessary. Therefore, it is possible to adjust the field of view of the imaging device, so it is possible to obtain various items of X-ray image information.

In the embodiments described above, the case of rotating and/or adjusting the position of one of an X-ray detector and a collimator was described. As another example, it may be possible to rotate and/or adjust both of an X-ray detector and a collimator, in which the rotational directions and the position adjustment direction of them may be the same of different.

According to the embodiments of the present invention described above, it is possible to rotate and/or adjust the position of at least one of an X-ray detector and a collimator that are main components of an X-ray imaging device. That is, it is possible to rotate and/or adjust the position of one of an X-ray detector and a collimator relative to the other.

Accordingly, it is possible to adjust the X-ray detection area, if necessary. Therefore, it is possible to adjust the field of view of the imaging device, so it is possible to obtain various items of X-ray image information.

The invention claimed is:

1. An X-ray imaging device comprising:
   an X-ray generator for generating an X-ray;
   an X-ray detector for detecting an X-ray generated by the X-ray generator and passing through an object; and
   a collimator disposed between the X-ray generator and the X-ray detector,
   wherein at least one of the X-ray detector or the collimator is rotated relative to the X-ray generator.

2. The X-ray imaging device of claim 1, wherein at least one of the X-ray detector and the collimator is rotated about a rotation axis directing the X-ray generator.

3. The X-ray imaging device of claim 2, wherein at least one the rotation axis and the X-ray detector or the rotation axis and the X-ray generator maintains an angle that exceeds 0 degree and is 90 degrees or less.

4. The X-ray imaging device of claim 2, wherein at least one of angles made by the rotation axis and the X-ray detector or the rotation angle and the X-ray generator is fixed or changed during imaging.

5. The X-ray imaging device of claim 1, wherein the relative rotation is made while X-ray imaging is performed, or until imaging is finished from before X-ray imaging.

6. The X-ray imaging device of claim 1, wherein the X-ray detector or the collimator is adjusted in position in a height direction or a width direction relative to the X-ray generator.

7. The X-ray imaging device of claim 1, wherein a rotation axis for the relative rotation is positioned inside the X-ray detector or the collimator.

8. The X-ray imaging device of claim 1, comprising a rotary arm having the X-ray generator and the X-ray detector at both ends and rotating.

9. The X-ray imaging device of claim 1, wherein both of the X-ray detector and the collimator are rotated about a rotation axis directing the X-ray generator.

10. The X-ray imaging device of claim 1, wherein the X-ray imaging device produces at least one of a CT image, a panoramic image, and a cephalometric image.

* * * * *